(12) United States Patent
Zegarelli et al.

(10) Patent No.: US 6,185,740 B1
(45) Date of Patent: Feb. 13, 2001

(54) DISPOSABLE PATIENT FACIAL MASK

(76) Inventors: Peter J. Zegarelli, 11 Raafenberg Rd., Pocantico Hills, NY (US) 10591; Mitchell Steinberg, 85 Coves Run, Oyster Bay Cove, NY (US) 11791

(*) Notice: Under 35 U.S.C. 154(b), the term of this patent shall be extended for 0 days.

(21) Appl. No.: 09/603,861

(22) Filed: Jun. 26, 2000

(51) Int. Cl.[7] .................................................. A42B 1/00
(52) U.S. Cl. ........................ 2/9; 2/206; 128/206.19; 128/206.21; 128/857
(58) Field of Search ................... 2/9, 206; 128/857.859, 128/206.19, 206.21, 206.24, 206.25, 206.28, 207.11, 207.13, 200.29, 201.15; 433/136, 137

(56) References Cited

U.S. PATENT DOCUMENTS

| | | | |
|---|---|---|---|
| 4,344,758 | * 8/1982 | Wielhouwer et al. | 433/137 |
| 4,889,490 | * 12/1989 | Jenkinson | 433/136 |
| 5,140,997 | * 8/1992 | Glassman | 128/849 |
| 5,303,423 | * 4/1994 | Gazzara et al. | 2/9 |
| 5,424,787 | * 6/1995 | Zegarelli | 351/111 |
| 5,694,925 | * 12/1997 | Reese et al. | 128/206.19 |
| 5,927,280 | * 7/1999 | Miyake | 128/857 |
| 6,079,980 | * 6/2000 | Durand | 433/137 |

* cited by examiner

Primary Examiner—Gloria M. Hale
(74) Attorney, Agent, or Firm—Myron Amer P.C.

(57) ABSTRACT

A tissue face mask similar to that used by a dentist but placed in covering relation over the face of a patient preparatory to an abrasive dental procedure in which mask there are shaping stays that are manually conformed to the facial features of the patient to prevent harm to the patient from the particulate fall out of the abrasive dental procedure.

3 Claims, 1 Drawing Sheet

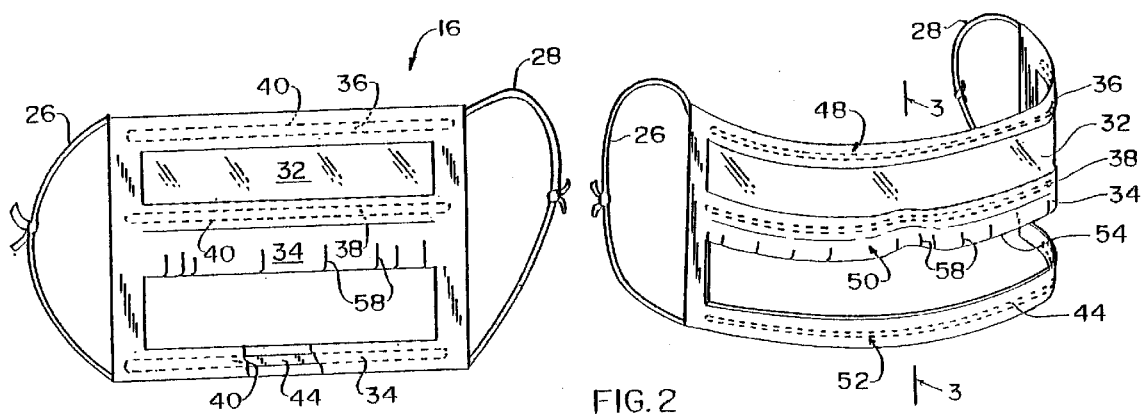
FIG. 1
FIG. 2
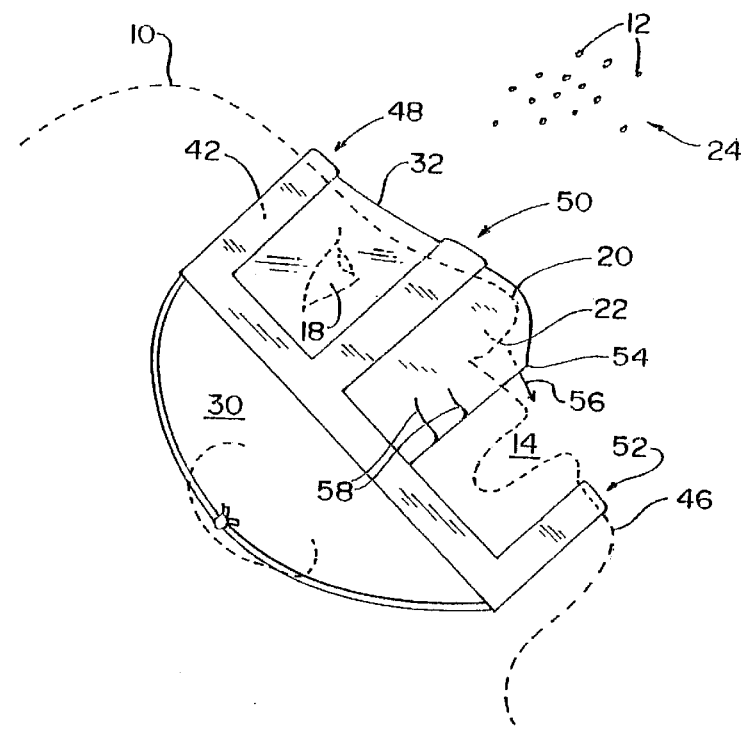
FIG. 3

DISPOSABLE PATIENT FACIAL MASK

The present invention relates generally to protective face masks, and more particularly to face masks primarily for dentistry practice.

EXAMPLES OF THE PRIOR ART

In U.S. Pat. No. 5,303,423 for Face Shield/Mask Combination issued to Gazzara et al. on Apr. 19, 1994, there is provided for use during medical procedures for the protection of medical personnel who, during such procedures, are subject to blood and other bodily fluids coming into contact with their face, a suitable face mask to obviate such contact, it being explained that such contact is dangerous because of the potential presence of the deadly AIDS virus or other harmful pathogens.

Thus, in dentistry practice, a face mask is used to obviate disease transmission between a patient and dentist, and the dentist, the user of the face mask, will dispose of the face mask between dental procedures to obviate disease transmission between patients. To facilitate the use of the face mask, used without exception by the dentist, the elimination of the discomfort of the elastic ear loops is the thrust of U.S. Pat. No. 5,424,787 for Eyeglasses With Mask Support Attachment Means issued to Peter J. Zegarelli, a coinventor of the present invention, on Jun. 13, 1995, and exemplifies the prior art effort concerned with the face mask for the dentist's use.

Underlying the present invention is the recognition that often the dental procedure provided the patient will entail the use of an air abrasion system, one such exemplary system being one using alumna powders of 27 to 50 microns and which gives rise to a fine particulate in surrounding relation about the patient which, without adequate protection provided to the patient, could get into the patient's nose and eyes with possible harmful consequences.

Broadly, it is an object of the present invention to provide a face mask affording protection to the patient, thus addressing a shortcoming of the prior art.

More particularly, it is an object to provide a dental patient's face mask affording effective protection against airborne micron-sized particulate.

The description of the invention which follows, together with the accompanying drawings should not be construed as limiting the invention to the example shown and described, because those skilled in the art to which this invention appertains will be able to devise other forms thereof within the ambit of the appended claims.

FIG. 1 is a front elevational view of a dental face mask used for patient protection in accordance with the present invention;

FIG. 2 is an isolated perspective view of the face mask illustrating the typical shape configurations of the stay constituents thereof contributing to the fit of the face mask; and FIG. 3 is side elevational view of the face mask in use over a patient's face and in section taken along line 3—3 of FIG. 2.

Part of the preparation of a patient 10 for protection against harmful consequences of airborne particulate, noted at 12, which is urged inadvertently in movement from a patient's mouth 14 during a dental abrasive procedure to a clearance position above the patient, as illustrated in FIG. 3, is the prone, or nearly prone, positioning of the patient 10 in a chair head support and thus in an upwardly facing relation.

Unlike the dentist's face mask, the patient's face mask 16 is horizontally, rather than vertically, oriented in covering relation over the area to be protected. namely, the eyes 18 and nose 20, and thus the nostrils 22, into which the particulate 12 poses the potential of entering after a gravity descent from the location 24. The positioning elastic loops 26 and 28 are used, but are not as essential as in the use of the dentist's face mask.

Because the source of the particulate 12 is typically alumna powder of 27 to 50 microns in size, the face mask 16 requires being imparted with a shape conforming as closely as possible to the shapes of the facial features of each patient 10 fitted with the face mask 16. To this end, face mask 16 is construction wise similar in many respects to a typical dentist's face mask, such as having its stock dimensions of 6 ¾ inches by 3 ½ inches, the former dimension possibly being increased to 8 inches in order to adequately cover the eyes 18 and extend to the patient's temple area 30, and also being sized for both adult and pedo usage.

In addition however, and in accordance with the present invention, the patient's face mask 16 has as constituent components an upper clear plastic panel 32, of a preferred minimal size of 1 inch by 6 inches, an appropriately attached depending tissue portion 34, of the same tissue construction material used in a dentist's face mask, and at least two horizontally oriented spaced apart shape-conforming stays 36 and 38 each of malleable metal construction material and each adhesively or otherwise appropriately contained within a stay-enclosing pocket or compartment 40. Stay 36 above the see-through panel 32, which panel 32 is coincident with the location of the patient's eyes 18, is coincident with the patient's forehead 42, and stay 38 below the panel 32 coincident with the location of the bridge of the patient's nose 20. In the embodiment selected for illustration, the face mask 16 includes an embodied third stay 44 coincident with the location of the patient's chin 46.

After placement of the face mask 16 in covering relation over the patient's face, the dentist or a dental assistant will manually shape the top stay 36 to the shape of the patient's forehead 42 and in a curvilinear configuration extending from one side temple 30 to the other, followed next by shaping stay 38 to a substantially inverted U-shape, a shape typical of a bridge of a nose, to the patient's nose, and lastly shaping stay 44 to the curvilinear shape of the patient's chin 46. The assumed noted shapes of the top, middle and bottom stays 36, 38 and 44 are respectively depicted at 48, 50 and 52 in FIG. 2, and in practice have been found to contribute to a good conforming fit of the face mask 16 to the unique facial shape of the patient 10, effective against the passage of even the microscopic sized particulate 12 from bypassing the facial mask 16 in its advantageous interposed position between the source site 24 and the prone patient 10.

In some instances, the bottom edge 54 of the tissue portion 34 will be pulled down, a degree of movement 56 allowed by the pleat construction 58 of the tissue portion 34 so that the bottom edge 54 serves as an effective closure for the patient's nostrils 22.

While the face mask for practicing the within inventive method, as well as said method herein shown and disclosed in detail is fully capable of attaining the objects and providing the advantages hereinbefore stated, it is to be understood that it is merely illustrative of the presently preferred embodiment of the invention and that no limitations are intended to the detail of construction or design herein shown other than as defined in the appended claims.

What is claimed is:

1. For patient preparation to provide protection against airborne abrasive powders of micron dimensions used in a dental abrasive procedure, an improved method of obviating a harmful consequence thereof comprising the steps of:

(1) positioning prone on a support a patient facing upwardly in relation to a potential source of airborne abrasive powder of micron dimensions;

(2) using a face mask constituent with an upper clear plastic portion, a depending tissue lower portion, and at least two horizontally oriented spaced apart shape-conforming stays of malleable metal construction material on opposite sides of said plastic panel;

(3) placing said aforesaid constituent face mask in covering relation over said patient's face with said plastic portion coincident with the eyes of said patient and said tissue portion over said patient's nose; and (4) manually shaping each said shape-conforming stay respectively to the underlying shapes of the forehead and nose of said patient;

whereby harm is obviated by said interposed position of said face mask between said prone patient and said source of airborne abrasive power.

2. The method of patient preparation as claimed in claim 1 wherein said abrasive powder is alumna of 27 to 50 microns.

3. The method of patient preparation as claimed in claim 1 wherein said face mask is constituent with a third horizontally oriented stay of malleable metal construction material in overlying relation to the chin of the patient.

* * * * *